(12) United States Patent
Cerqueira et al.

(10) Patent No.: US 10,729,812 B2
(45) Date of Patent: Aug. 4, 2020

(54) HUMAN NIPPLE AREOLAR COMPLEX EXTRACELLULAR MATRIX SCAFFOLD AND METHODS RELATING THERETO

(71) Applicant: NOVOTHELIUM, LLC, San Antonio, TX (US)

(72) Inventors: Bianca G. Cerqueira, San Antonio, TX (US); Lauren E. Cornell, San Antonio, TX (US)

(73) Assignee: NovoThelium, LLC, San Antonio, TX (US)

( * ) Notice: Subject to any disclaimer, the term of this patent is extended or adjusted under 35 U.S.C. 154(b) by 236 days.

(21) Appl. No.: 15/626,058

(22) PCT Filed: Dec. 9, 2016

(86) PCT No.: PCT/US2016/066024
§ 371 (c)(1),
(2) Date: Jun. 17, 2017

(87) PCT Pub. No.: WO2017/100713
PCT Pub. Date: Jun. 15, 2017

(65) Prior Publication Data
US 2018/0177917 A1 Jun. 28, 2018

Related U.S. Application Data

(60) Provisional application No. 62/265,798, filed on Dec. 10, 2015.

(51) Int. Cl.
*A61L 27/36* (2006.01)
*A61L 27/38* (2006.01)
*A61F 2/12* (2006.01)

(52) U.S. Cl.
CPC ............ *A61L 27/3633* (2013.01); *A61F 2/12* (2013.01); *A61L 27/3666* (2013.01);
(Continued)

(58) Field of Classification Search
CPC ............. A61L 27/3633; A61L 27/3687; A61L 27/3666; A61L 27/3869; A61L 2430/04; A61F 2/12
See application file for complete search history.

(56) References Cited

U.S. PATENT DOCUMENTS 9,150,318 B1 † 10/2015 Sun
2013/0013068 A1   1/2013 Forsell et al.
2015/0157451 A1   6/2015 Bowley et al.

FOREIGN PATENT DOCUMENTS

WO        070162 A1 †  5/2016

OTHER PUBLICATIONS

Lu et al., Comparison of decellularization techniques for preparation of extracellular matrix scaffolds derived from three-dimensional cell culture. Journal of Biomedical Materials Research, vol. 100A, No. 9 (Sep. 2012) pp. 2507-2516. (Year: 2012).*

(Continued)

*Primary Examiner* — Kara D Johnson
(74) *Attorney, Agent, or Firm* — Dickinson Wright PLLC; Kristopher Lance Anderson

(57) ABSTRACT

Methods of producing and methods of treatment using a nipple areolar complex extracellular matrix. A method for processing tissue comprises harvesting a human nipple areolar complex tissue, treating the tissue with a stabilizing medium, wherein the medium stabilizes the tissue during transport, decellularizing the tissue, and sterilizing the tissue to form a human nipple areolar complex extracellular matrix scaffold (ECMS). A method of treating an individual with a need for a nipple reconstruction comprises forming an ECMS and applying the ECMS to the individual for nipple areolar regeneration.

15 Claims, 9 Drawing Sheets

(52) U.S. Cl.
CPC ....... *A61L 27/3687* (2013.01); *A61L 27/3869* (2013.01); *A61L 2430/04* (2013.01)

(56) References Cited

OTHER PUBLICATIONS

Officer Lee W. Young; Notification of Transmittal of the International Search Report and the Written Opinion of the International Searching Authority; PCT/US2016/066024; dated Apr. 10, 2017; 10 pages.

Nicholas C. Pashos et al.; A Tissue Engineered Nipple and Areola Complex; http://www.cell.com/molecular-therapy-family/molecular-therapy/fulltext/S1525-0016(16); The American Society of Gene & Cell Therapy; vol. 23, Supplement 1, pp. 254-255, May 2015, printed Apr. 28, 2017, 2 pages.

W. Siggelkow; Skin-Reducing Mastectomy with Primary Implant Reconstruction; https://www.ncbi.nlm.nih.gov/pmc/articles/PMC4168326/; Geburtshilfe und Frauenheilkunde; Jul. 2012; 72(7): 616-621, printed Apr. 28, 2017, 8 pages.

Gálvez-Montón et al. May 27, 2015. Neoinnervation and neovascularization of acellular pericardial—derived scaffolds in myocardial infarcts, Stem Cell Research & Therapy 6:108.†

Pashos et al. May, 2015. A Tissue Engineered Nipple and Areola Complex. Molecular Therapy vol. 23, Supplement 1, p. S254-S255.†

Bonvillain, et al. Aug. 23, 2012. A nonhuman primate model of lung regeneration: detergent-mediated decellularization and initial in vitro recellularization with mesenchymal stem cells. Tissue Eng Part A. 18(23-24): 2437-52.†

\* cited by examiner
† cited by third party

FIG. 6A
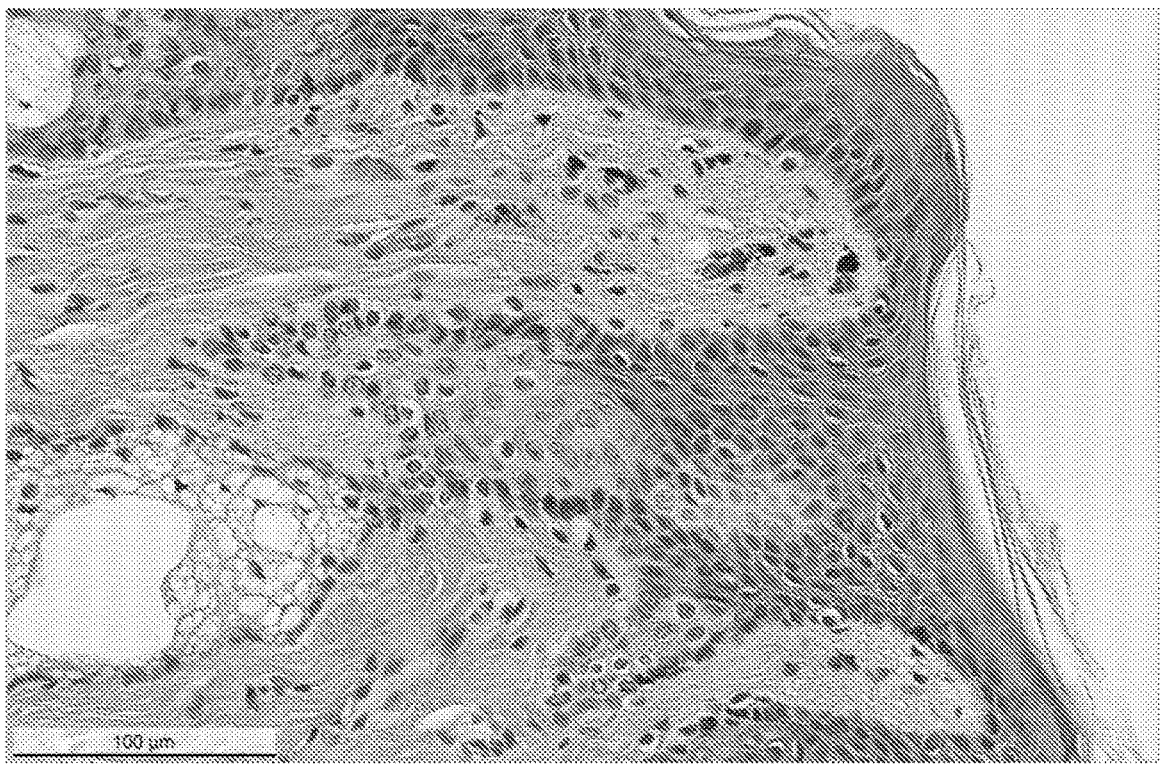
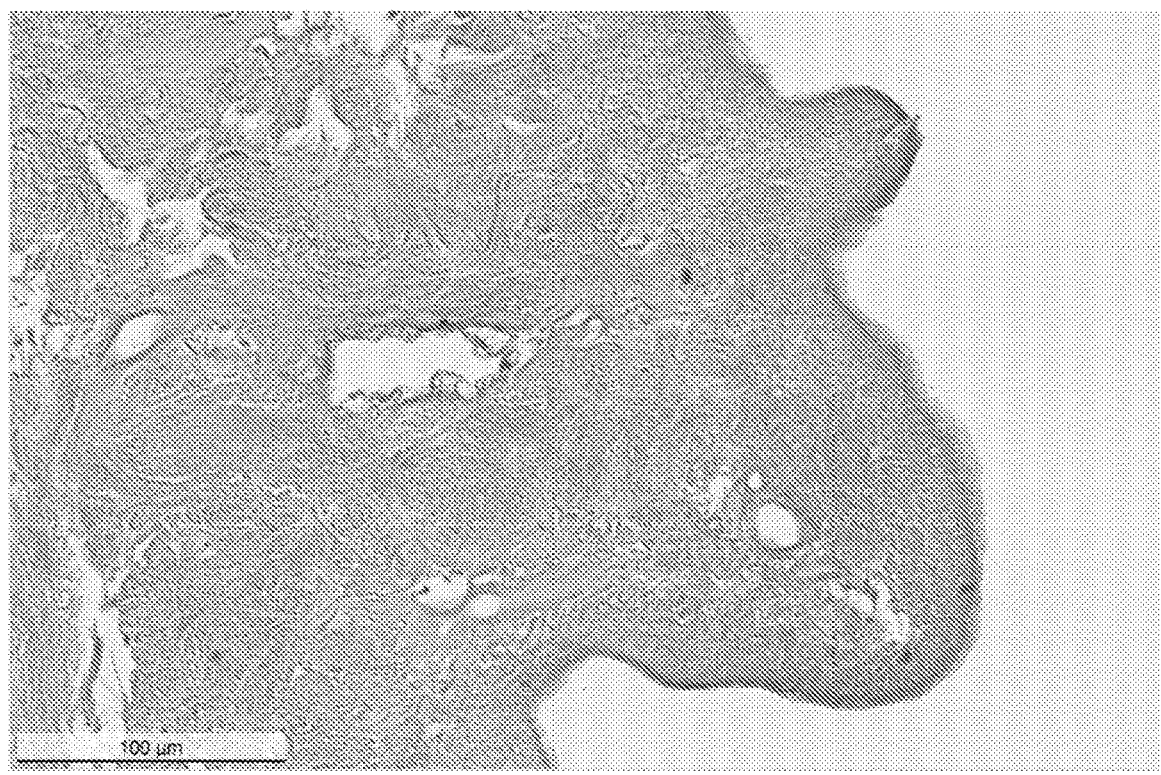
FIG. 6B

FIG. 7A
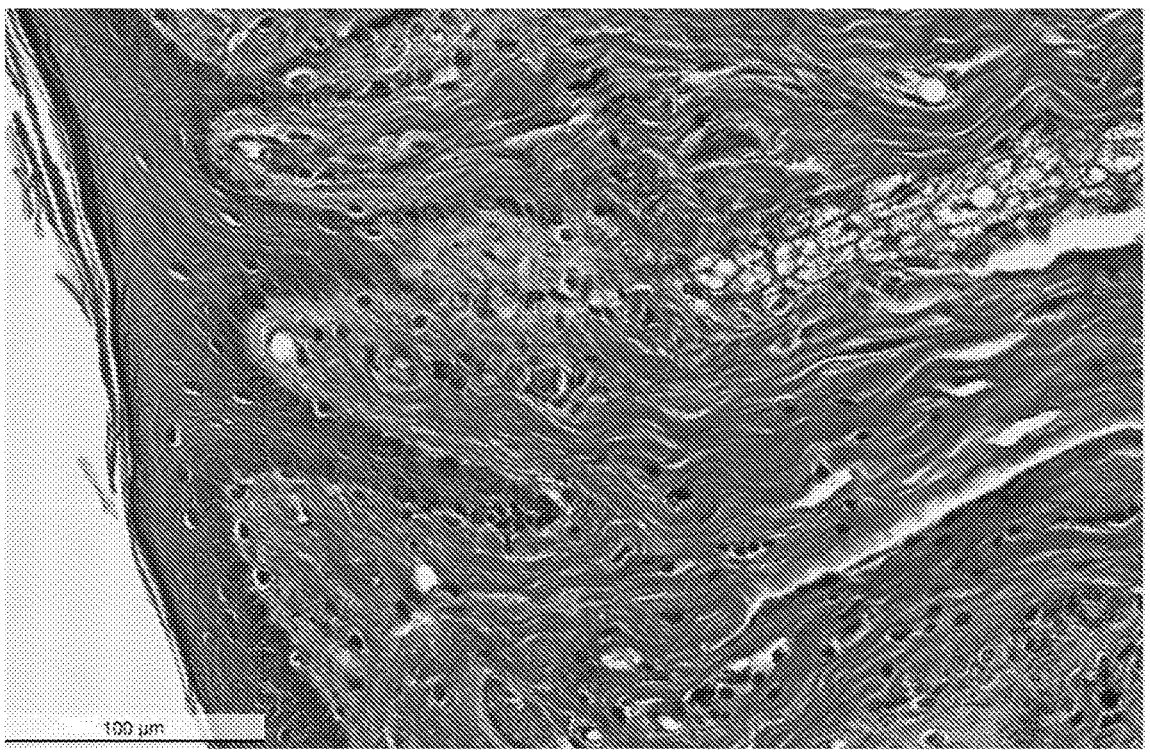
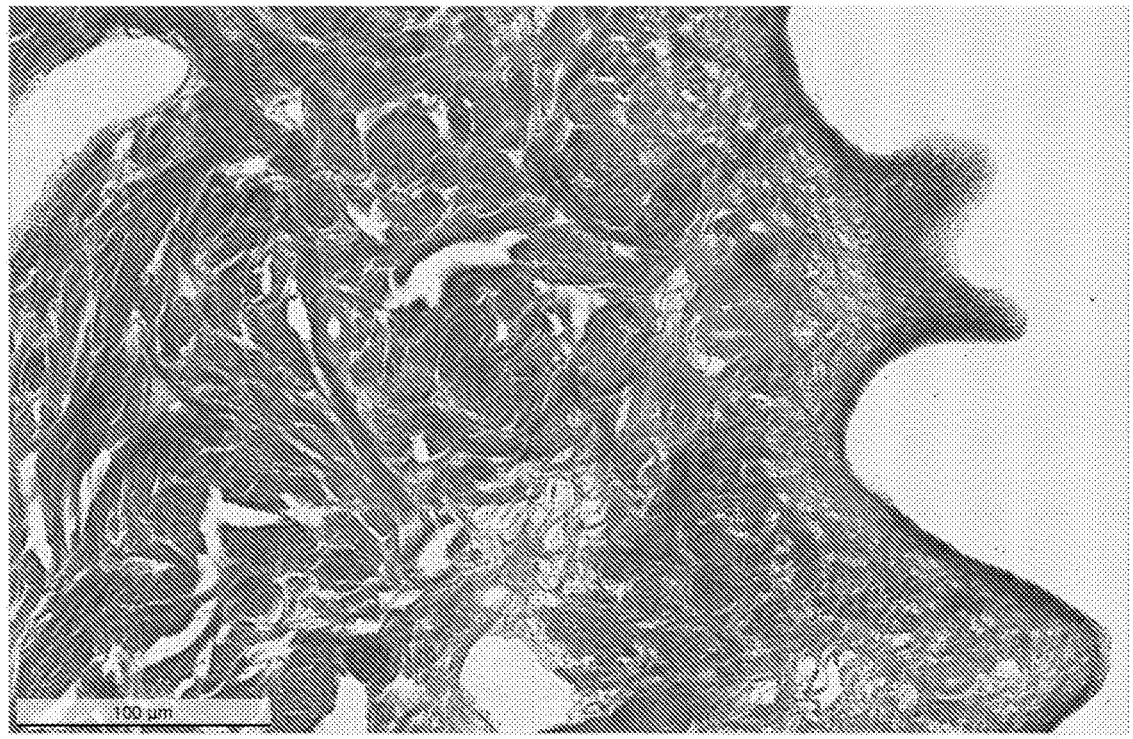
FIG. 7B

FIG. 7C
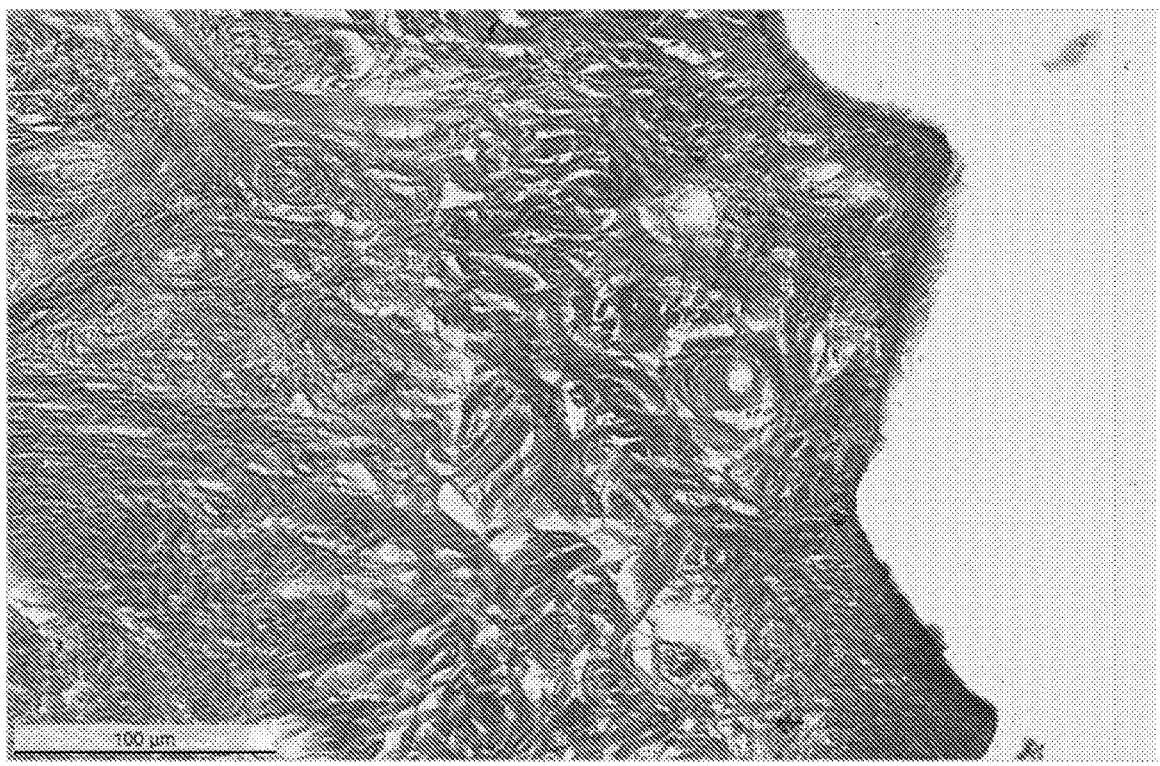
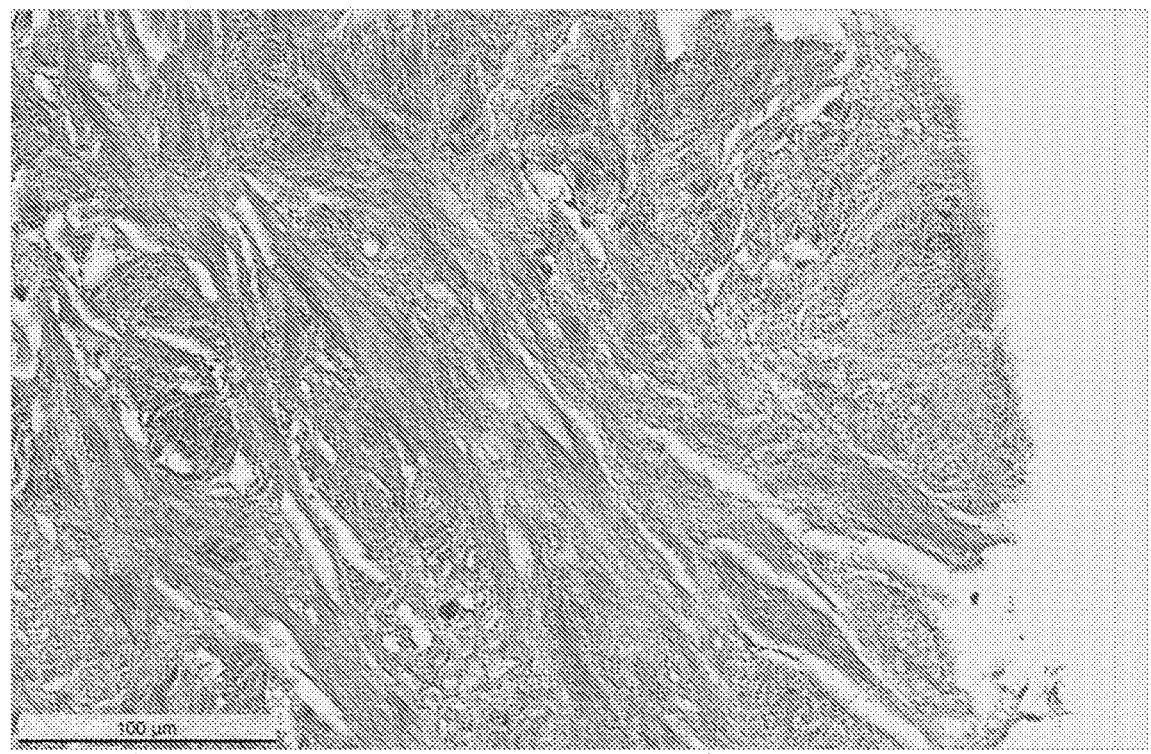
FIG. 7D

| NATIVE HUMAN NIPPLE TISSUE | HUMAN NIPPLE ECM |
|---|---|
  |  FIG. 8E |
  |  FIG. 8F |
  |  FIG. 8G |
  |  FIG. 8H |

HUMAN NIPPLE AREOLAR COMPLEX EXTRACELLULAR MATRIX SCAFFOLD AND METHODS RELATING THERETO

This application includes material that is subject to copyright protection. The copyright owner has no objection to the facsimile reproduction by anyone of the patent disclosure, as it appears in the Patent and Trademark Office files or records, but otherwise reserves all copyright rights whatsoever.

CROSS-REFERENCE TO RELATED APPLICATIONS

This application is a national phase filing of PCT/US2016/066024, filed on Dec. 9, 2016, entitled "Human Nipple Areolar Complex Extracellular Matrix Scaffold And Methods Relating Thereto" which claims priority to U.S. Patent Application Ser. No. 62/265,798, filed Dec. 10, 2015, entitled "Nipple Areolar Complex Extracellular Matrix Scaffold". The foregoing patent applications are hereby incorporated by reference in their entirety for all purposes.

FIELD

The present invention is related to the creation of an extracellular matrix scaffold from autologous or allograft tissue for use in human nipple areola tissue regeneration, reconstruction, or replacement.

BACKGROUND

Nipple areolar reconstruction is desired in individuals whom have lost a nipple due to cancer, trauma, or congenital absence. Current options for nipple reconstruction include recreating the appearance of a nipple by a prosthetic silicone nipple that is adhered to the skin of the breast mound, surgical reconstruction with or without tattoo to match natural nipple pigmentation, or a tattoo of a nipple.

Surgical reconstruction may be performed using a composite nipple graft from the contralateral nipple, a local skin flap, skin flaps with autologous graft augmentation, skin flaps with alloplastic augmentation, or skin flaps with allograft augmentation.

Composite nipple grafts use a portion of the contralateral nipple as a tissue graft for the nipple reconstruction. This type of reconstruction requires a contralateral nipple with adequate volume to accommodate a donation to the other side. There is also risk of donor site morbidity, nipple discoloration, and loss of sensation of the donor nipple.

Local skin flaps are most commonly used to recreate the appearance of a nipple. Loss of projection occurs in all nipples created from surgical flaps, due to retraction forces of the underlying tissue and contraction of scar tissue. To address loss of projection, surgical flaps may be augmented with autologous tissue such as cartilage or fat. Autologous tissue donation requires a secondary surgical site with risk of donor site morbidity. Surgical flaps may also be augmented with alloplastic substances such as silicone gel, hyaluronic acid, calcium hydroxylapatite (RADIESSE™), hydroxyapatite and tricalcium phosphate (CERATITE™), and polytetrafluoroethylene (PTFE). A major disadvantage of alloplastic augmentation is risk of infection and or extrusion of the substance.

Xenograft tissue such as extracellular collagen matrix derived from porcine small intestinal mucosa (Cook medical nipple reconstruction cylinder) may also be used to augment surgical flaps. However, this type of material may not be used in individuals with sensitivity to porcine material or with irradiated skin. Acellular dermal allografts have been used to augment surgical flaps. Allograft tissue has a higher rate of incorporation with limited resorption, reducing risk of infection and or extrusion. Maintained structure and biochemistry of the tissue matrix allows for tissue integration into the graft, with native cells repopulating the matrix.

All surgical flap reconstructed nipples will flatten by 50-75% over 2 years. In approximately 10-15% of reconstructions, the nipple will lose all projection. The most common reason for dissatisfaction following nipple-areolar reconstruction is lack of projection, followed by color match, shape, size, texture and position. Only 13% of all patients were totally satisfied with their reconstructed nipple areolar complex. Factors that may negatively affect projection include external pressure on the reconstruction, poor surgical design, thin skin and dermis, and lack of subcutaneous fat.

All current methods of nipple reconstruction only recreate the appearance of a nipple. The nipple is a site of specialized epidermis since it is glabrous, associated with a unique gland (mammary), has distinct patterns of epidermal stratification, and expresses unique differentiation markers that are not present in trunk epidermis. During lactation, the nipple undergoes high mechanical strain as well as prolonged exposure to high moisture and digestive enzymes in saliva. In humans, the nipple has approximately 15-20 lactiferous ducts centrally located that are lined mainly by a two-layered stratified cuboidal epithelium. Tightly packed collagen bundles surround the ducts as well as smooth muscle that is oriented parallel and circular to the ducts. The nipple has deep infolding of the epidermis into an extensive papillary dermis with fine collagen bundles. The human areola has similar invaginations of the epidermis, although less dramatic. The human areola has large sebaceous glands called Montgomery's tubercles that are thought to prevent sore or chapped nipples and secrete pheromone substances that aid in nursing. The human nipple areolar complex is more pigmented than surrounding skin with melanocytes abundant not only in the epidermis, but also in the basal layer of the sebaceous gland and lactiferous ducts. It is thought that the growth factor environment of the nipple areolar complex (NAC) tissue promotes melanocyte survival in areas where they are typically not found.

Despite efforts to recreate cosmetic solutions for NAC tissue replacement, there remains a significant need in the art for human NAC replacements capable of reproducing the complex physiological and morphological characteristics of a human NAC.

SUMMARY OF THE DISCLOSURE

It is therefore an object of the present invention to provide a human nipple areolar complex extracellular matrix scaffold from autologous or allograft human nipple areolar tissue for use in human nipple reconstruction, regeneration, or replacement.

In one aspect of the present invention, a method for processing tissue comprises harvesting a human nipple areolar complex tissue, treating the tissue with a stabilizing medium, wherein the medium stabilizes the tissue during transport, decellularizing the tissue, and sterilizing the tissue to form a human nipple areolar complex extracellular matrix scaffold (ECMS). In some embodiments, the harvesting step comprises harvesting the tissue from a cadaver. In some embodiments, the harvesting step comprises harvesting the tissue from an individual during a surgery.

In another aspect of the present invention, a method of treatment comprises identifying an individual with a need for a nipple reconstruction, forming a human nipple areolar complex extracellular matrix scaffold (ECMS), and applying the ECMS to the individual. The forming comprises harvesting a human nipple areolar complex tissue, treating the tissue with a stabilizing medium, wherein the medium stabilizes the tissue during transport, decellularizing the tissue, and sterilizing the tissue to form an ECMS. In some embodiments, the individual is an individual who has lost a nipple due to a cancer, a trauma, or a congenital absence. In some embodiments, the individual is an individual seeking a new nipple for a cosmetic reason. In some embodiments, the applying step comprises direct implantation of the ECMS onto the individual for in vivo cellular repopulation using the individual's cellular responses. In some embodiments, the method further comprises, before the applying step, recellularizing the ECMS to yield a recellularized ECMS, wherein the applying step comprises applying the recellularized ECMS to the individual.

It is therefore an object of the present invention to provide a method for regenerating a nipple areolar complex comprising: harvesting a nipple areolar complex tissue; treating the tissue with a stabilizing medium, wherein the medium stabilizes the tissue during a transport; and decellularizing the tissue; wherein a nipple areolar complex extracellular matrix scaffold (ECMS) is produced comprised of at least dermal or subdermal layers. In another aspect a further step comprises sterilizing the nipple areolar complex ECMS. In another aspect the harvested nipple areolar complex is human and may be harvested tissue from a cadaver or from an individual during a surgery.

In another aspect, the decellularizing step comprises decellularization using one or more decellularization methods selected from the group consisting of: detergents, enzymes, salts, electrophoresis, and combinations thereof. An additional step includes after application of the nipple areolar complex ECMS to an individual, the scaffold is repopulated by cells in vivo. In another aspect the present invention comprises repopulating the nipple areolar complex ECMS with exogenous cells selected from the group consisting of: fibroblasts, epithelial cells, mammary endothelial cells, mammary epithelial cells, vascular smooth muscle cells, bone marrow mesenchymal stem cells, adipose derived stem cells, induced pluripotent stem cells, or combinations thereof.

In another aspect of the present invention, a method of treatment comprises: identifying an individual with a need for a nipple reconstruction; forming a nipple areolar complex extracellular matrix scaffold (ECMS), the forming comprising; harvesting a nipple areolar complex tissue; treating the tissue with a stabilizing medium, wherein the medium stabilizes the tissue during transport; decellularizing the tissue to yield a sterile nipple areolar complex ECMS comprising at least dermal or subdermal layers; and applying the nipple areolar complex ECMS to the individual.

The method of the present invention may be performed for an individual who has lost a nipple due to a cancer, a trauma, congenital absence, or a cosmetic reason. In another aspect, the harvested nipple areolar complex tissue is human nipple areolar complex tissue.

In another aspect, direct implantation of the ECMS onto the individual is performed. The implanted decellularized ECMS may be repopulated naturally by the patient's native cells, or may be populated by recellularizing the ECMS to yield a recellularized ECMS, and wherein the applying step comprises applying the recellularized ECMS to the individual.

Such a recellularization step may further comprise recellularizing the nipple areolar complex ECMS with exogenous cells selected from the group consisting of: fibroblasts, epithelial cells, mammary endothelial cells, mammary epithelial cells, vascular smooth muscle cells, bone marrow mesenchymal stem cells, adipose derived stem cells, induced pluripotent stem cells, or combinations thereof.

It is another object of the present invention to provide a nipple areolar complex extracellular matrix scaffold (ECMS), comprising a decellularized nipple areolar complex ECMS, wherein the nipple areolar complex ECMS is capable of supporting regeneration of a nipple areolar complex when applied to a patient. The nipple areolar complex ECMS may be derived from human nipple areolar tissue and may further be capable of supporting growth of melanocytes. The nipple areolar complex ECMS of the present invention comprises at least dermal layers.

In one aspect, the present invention has the potential for increased sensation of the nipple area complex occurring within 2 years of ECMS incorporation and may further exhibit maintained projection of the nipple, retained structure after processing.

In one aspect of the present invention, the nipple areolar complex ECMS does not illicit a negative immune response when exposed to a recipient's cells. The nipple areolar complex ECMS may be applied to an individual, and is capable of generating pigmentation of the nipple area complex.

BRIEF DESCRIPTION OF THE DRAWINGS

The present invention is further described in the detailed description which follows, in reference to the noted plurality of drawings by way of non-limiting examples of exemplary embodiments, in which like reference numerals represent similar parts throughout the several views of the drawings, and wherein:

FIG. 6A depicts a histological slice of native human nipple tissue at 200× magnification stained with hematoxylin and eosin.

FIG. 6B depicts a histological slice of human nipple ECM scaffold prepared using Example 1 methods at 200× magnification stained with hematoxylin and eosin.

FIG. 7A depicts a histological slice of native human nipple tissue at 200× magnification stained with Trichrome Stain.

FIG. 7B depicts a histological slice of human nipple ECM scaffold prepared using Example 1 methods at 200× magnification stained with Trichrome Stain.

FIG. 7C depicts a histological slice of human nipple ECM scaffold prepared using Example 2 methods at 200× magnification stained with Trichrome Stain.

FIG. 7D depicts a histological slice of human nipple ECM scaffold prepared using Example 2 methods at 200× magnification stained with Trichrome Stain.

Figure 1:
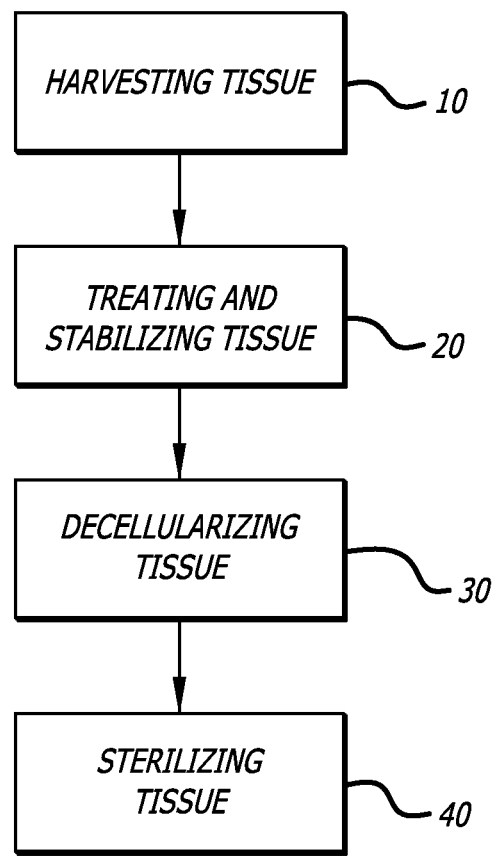
FIG. 1 depicts a flow chart of an embodiment of a method of fabricating a human nipple areolar complex extracellular matrix scaffold from human nipple areolar complex tissue.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the instant disclosure may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The present invention presents a novel nipple areolar complex (NAC) and method for NAC replacement by utilizing a tissue-engineered extracellular matrix scaffold created from human nipple areolar tissue to enable the patient to regenerate an anatomical nipple made from her own cells. By using an extracellular matrix derived from human nipple areolar tissue, the NAC of the present invention maintains the unique structural and growth factor environment of the nipple.

Previous in vitro data indicates that the removal of cellular components from native tissues leaves behind a complex protein matrix, designated extracellular matrix, which can provide cells a combination of cues that closely resemble the in vivo environment in vitro. Recent studies have suggested that superior function and complex tissue formation occurred when ECM scaffolds were derived from site-specific homologous tissues compared with heterologous tissues.

In some embodiments of the present invention there are disclosed methods for processing or fabricating a human nipple areolar complex extracellular matrix scaffold (ECMS).

In another embodiment of the present invention, proteins remain behind in the scaffold (that aid in cellular in growth) following the decellularization process. The ability for the human nipple areolar complex ECMS of the present invention to result in a patient's reformation of a nipple areolar complex as opposed to current methods such as tattoos or nipple flap creation, such reformation including additional benefits such as enhanced stimuli response (like ability of nipple to harden when exposed to temp changes or sensual stimuli) of the nipple areolar complex ECMS of the present invention versus traditional nipple flap creation. While limited, increase of sensation of the nipple areolar complex is realized when utilizing the nipple areolar complex ECMS of the present invention. In yet another embodiment of the present invention, the reformed nipple areolar complex utilizing the nipple areolar complex ECMS of the present invention results in increased projection as compared to traditional nipple areolar flap creation, as well as increasing potential for pigmentation as compared to nipple areolar flap creation. The scaffolding network of the nipple areolar complex ECMS allows for formation of actual nipple versus scar/tattoo, including texture, projection and pigmentation.

Figure 2:
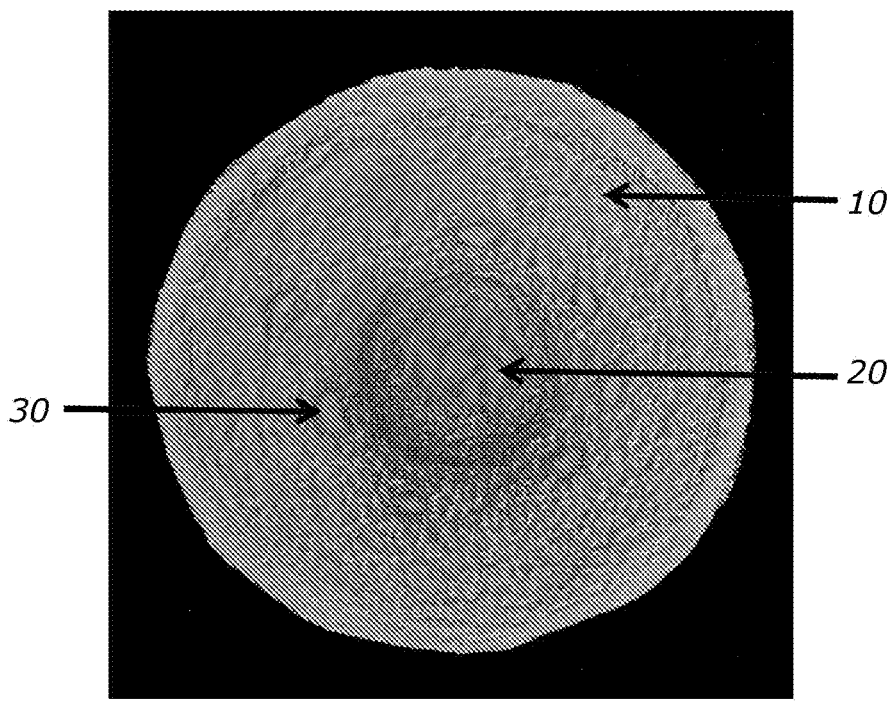
FIG. 2 depicts an embodiment of native human nipple areolar complex tissue.
Figure 3:
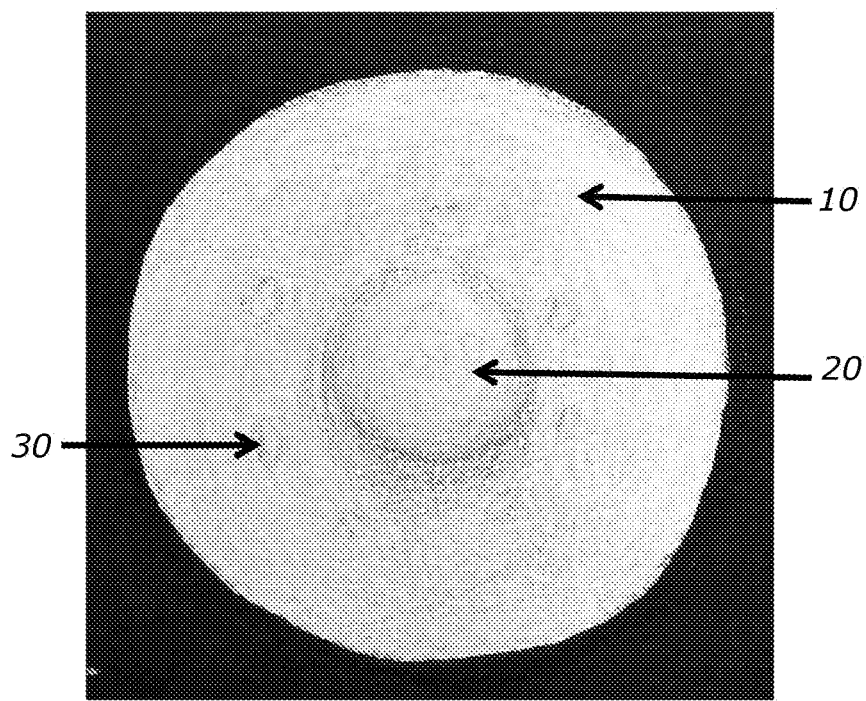
FIG. 3 depicts an embodiment of an acellular human nipple areolar complex extracellular matrix scaffold (ECMS) originating from the same human native nipple areolar complex in FIG. 2.

Referring now to FIG. 1, the method comprises the steps of harvesting human nipple areolar complex tissue 10, treating the tissue with a stabilizing medium 20, the stabilizing medium configured to prepare the tissue for transport to a processing center, decellularizing the tissue 30 to form a nascent scaffold, and sterilizing the scaffold 40 to yield a human nipple areolar complex extracellular matrix scaffold (ECMS) from the tissue. As seen in FIG. 2 and FIG. 3, both the native human nipple areolar complex and the ECMS derived from said complex demonstrate characteristics of native human nipple areolar complexes, specifically a projecting nipple and areola.

Harvesting the tissue 10 may comprise harvesting human nipple tissue from cadavers under standard processes of tissue procurement. Harvesting may be done in coordination with a tissue procurement company or a tissue bank. A donor nipple may be harvested preferably under aseptic conditions less than 48 hours after death with a dermatome, and maintained at low temperature, preferably no warmer than 4° C. In an exemplary embodiment, human nipple tissue is subject to minimum tissue requirements, including but not limited to: no previous indication of breast cancer or irradiation in breast as well as donor testing for infectious agents, such as HIV, Hepatitis C, and Hepatitis B, as recommended by the American Association of Tissue Banks.

Following harvesting 10, the tissue is treated and stabilized 20 for transport with a stabilizing solution. The stabilizing solution may (1) prevent osmotic, hypoxic, autolytic and proteolytic degradation to the tissue, (2) protect against microbial contamination of the tissue, and (3) reduce mechanical damage to the tissue. The stabilizing solution may comprise one or more of a buffer, antioxidants, oncotic agents, protease inhibitors, antibiotics, and optionally a smooth muscle relaxant. The tissue may stay in the stabilizing solution for no more than 7 days, but ideally the tissue is transported by overnight delivery on wet ice to a tissue processing center.

After the tissue is stabilized 20 and transported to a processing facility, the tissue is decellularized 30. Historically, decellularization may be accomplished using a number of chemical treatments, including incubation in certain salts, detergents or enzymes. The use of the detergent TRITON X-100, a trademarked product of Rohm and Haas Company of Philadelphia, Pa., has been demonstrated to remove cellular membranes, as detailed in U.S. Pat. No. 4,801,299. Other acceptable decellularizing detergents include polyoxyethylene (20) sorbitan mono-oleate and polyoxyethylene (80) sorbitan mono-oleate (Tween 20 and 80), sodium deoxycholate, 3-[(3-chloramidopropyl)-dimethylammino]-1-propane-sulfonate, octyl-glucoside and sodium dodecyl sulfate.

The foregoing decellularization process is exemplary and is non-limiting with regard to the decellularization phase of the present invention. Alternatively, enzymes may be used to accomplish decellularization, including but not limited to dispase II, trypsin, and thermolysin. Trypsin and other non xeno-free enzymes may be used in preclinical studies as a comparison tool to compare decellularization efficiency. These enzymes react with different components of collagen and intercellular connections in achieving their effects. Dispase II attacks Type IV collagen, which is a component of the lamina densa and anchoring fibrils of the basement membrane. Thermolysin attacks the bulbous phemphigoid antigen in the hemidesmosome of the basal layer of keratinocytes. Trypsin attacks the desmosome complex between cells. Due to the proteolytic nature of these enzymes, care must be taken that cellular removal occurs without significant damage to the extracellular matrix, including the basement membrane complex. This is a function of concentration, time and temperature. If used for too long a time or at too high a concentration, dispase II for example can completely remove the basement membrane complex from the dermis.

For example, with human cadaver skin Dispase II at 1.0 units/ml for 90 minutes at 37° C. will remove all keratinocytes except the basal layer, while some damage is already occurring to the basement membrane complex. Thermolysin at 200 ug/ml for 30 minutes at 4° C. will essentially remove all keratinocytes without damage to the basement membrane complex on some occasions, but this varies from donor to donor with evidence of basement membrane damage being seen in some donors. Incubation of skin in 1 molar sodium chloride for 16 hours for human skin and 48 hours for porcine skin will routinely allow clean separation of the epidermis and dermis without damage to the basement membrane complex.

In addition to salts, detergents and enzymes, the processing solution also contains certain protease inhibitors, to prevent degradation of the extracellular matrix. Collagen-based connective tissues contain proteases and collagenases as endogenous enzymes in the extracellular protein matrix. Additionally, certain cell types including smooth muscle cells, fibroblasts and endothelial cells contain a number of these enzymes inside vesicles called lysosomes. When these cells are damaged by events such as hypoxia, the lysosomes are ruptured and their contents released. As a result, the extracellular matrix can undergo severe damage from protein, proteoglycan and collagen breakdown. This damage may be severe, as evidenced in clinical cases of cardiac ischemia where a reduction in oxygen which is insufficient to cause cell death results in pronounced damage to the collagen matrix. Additionally, a consequence of extracellular breakdown is the release of chemoattractants, which solicit inflammatory cells, including polymorphonuclear leukocytes and macrophages, to the graft, which are intended to remove dead or damaged tissue. These cells also, however, perpetuate the extracellular matrix destruction through a nonspecific inflammatory response. Accordingly, the processing solution contains one or more protease inhibitors selected from the group of N-ethylmaleimide (NEM), phenylmethylsulfonylfluoride (PMSF) ethylenediamine tetraacetic acid (EDTA), ethylene glycol-bis-(2-aminoethyl (ether)NNN'N'-tetraacetic acid, ammonium chloride, elevated pH, apoprotinin and leupeptin to prevent such damage.

In addition to salts, detergents, enzymes and protease inhibitors, the processing solution generally contains an appropriate buffer. This may involve one of many different organic buffers which are described above. The inventors prefer to use an organic buffer selected from the group consisting of 2-(N-morpholino)ethanesulfonic acid (MES), Tris (hydroxymethyl)aminomethane (TRIS) and (N-[2-hydroxyethyl]piperazine-N'-[2-ethanesulfonic acid] (HEPES). Alternatively, a low salt or physiological buffer including phosphate bicarbonate acetate citrate glutamate with or without glycine, may be more appropriate in certain applications. Low salt or physiological buffers are more able to support the infiltration of the graft with viable cells and hence are more relevant when cellular infiltration including neovascularization is essential to early survival of the graft as in transplanted dermal matrix.

As the processing solution may contain chemicals that would be irritating or inflammatory on transplantation, it is important that the processing solution be thoroughly rinsed from the tissue. In some embodiments, this washing occurs by rinsing in sufficient changes of appropriate buffer, until residues of the processing solution are reduced to levels compatible with transplantation. Alternatively, components of the processing solution may be neutralized by specific inhibitors, e.g., dispase II by ethylenediaminetetraacetic acid (EDTA) or trypsin by serum.

In some embodiments, decellularizing human nipple tissue 30 yields a decellularized extracellular matrix (ECM) of an existing human nipple tissue, the decellularized matrix aiding in the long-term maintenance of a reconstructed human nipple architectural structure. The ECM is a compilation of secretions from various cell types that make up each respective tissue and has been shown to aid in the cell proliferation, migration, and differentiation. Previous in vitro data indicates that the removal of cellular components from native tissues leaves behind a complex protein matrix, designated extracellular matrix, which can provide cells a combination of cues that closely resemble the in vivo environment in vitro. Recent studies have demonstrated that superior function and complex tissue formation occurs when ECM scaffolds were derived from site-specific homologous tissues compared with heterologous tissues. Therefore, preserving the composition and architecture of the human nipple areolar ECM during the process of decellularization 30 is of utmost importance.

Figure 4:
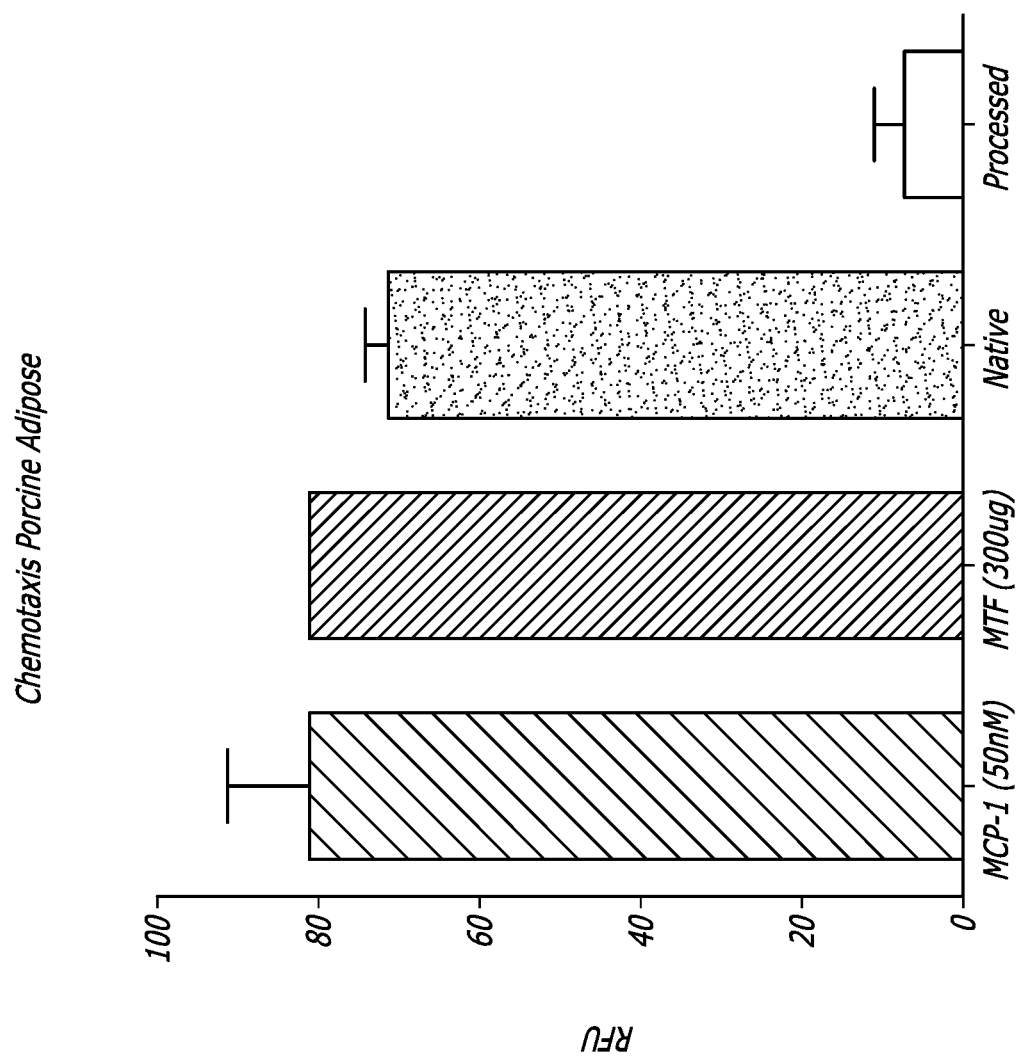
FIG. 4 depicts a graph showing Relative Fluorescent Units (RFU) measurement of native versus processed tissue to show decreased immune response when tissue is decellularized. MCP-1 (Monocyte Hemotactic Protein-1) is used as positive control.

Typically, when an allograft tissue is implanted, a strong immunological response occurs within the body. This immune reaction (mainly driven by monocytes) can cause rejection, necrosis and/or extrusion of the implanted material. However, when the allografts are stripped of native cell proteins and nucleic acids (not ECM proteins), the immune response is attenuated. Hence, the removal of native non-ECM cell proteins and nucleic acids from the allograft is used as a strategy to guarantee the successful integration of allografts, without eliciting strong immune reactions. An example of the reduced immune response through the process of decellularization as compared to native tissue can be seen in FIG. 4. FIG. 4 presents a graph showing Relative Fluorescent Units (RFU) measurement of native versus processed tissue, showing decreased immune response when tissue is decellularized. MCP-1 (Monocyte Hemotactic Protein-1) is used as positive control. MTF is a brand of commercially available acellular skin. Native is native porcine tissue. Processed is tissue processed to decellularize the tissue using similar methods claimed herein. Processed tissue shows decrease in monocyte chemoattraction (or immune response) as compared to all other materials.

In one embodiment, the human nipple areolar complex ECMS of the present invention exhibits reduced immunogenicity by utilization of a fully decellularized graft versus native tissue.

In order to reasonably ascertain whether decellularized tissue will elicit a strong negative immune reaction in human patients, a monocyte chemotactic assay was performed. Chemotaxis (migration) of human monocytes/macrophages, which are the first responders to tissue injury, were measured in decellularized versus native tissue adipose tissue to evaluate the response of these cells in vitro (see FIG. 4). When looking at decellularized tissue, chemo-attraction values of human monocytes (first responders to tissue injury) were significantly lower than those measured in native tissue, showing the decellularization process reduces innate immunogenicity.

Referring again to FIG. 1, decellularizing the tissue 30 comprises processing and preserving human nipple areolar tissue for transplantation, wherein the processing and preserving steps may comprise chemical pretreatment, cell removal, and sterilization, yielding a human nipple areolar scaffold. The processing step is designed to generate a transplantable biological tissue graft, wherein the graft (a) provides an extracellular matrix which can be regenerated and remodeled by the host, (b) does not elicit an negative immune response by the host, and (c) can be easily stored and transported. The preserving step may comprise incubating the tissue in a decellularizing solution configured to remove antigenic donor cells within the tissue. Decellularizing the tissue 30 may further comprise optimizing the concentration and time duration for cellular removal while preserving extracellular matrix integrity of the ECM. After the cells are thoroughly removed from the tissue, the tissue is washed several times to ensure removal of any remaining detergent or decellularizing solution. Decellularization of the tissue 30 may be verified by visualizing nuclear material in tissue sections stained with 4', 6-diamidino-2-phenylindole (DAPI) or hematoxylin and eosin (H&E). Additionally, remaining double stranded DNA can be quantified. Decellularizing solutions may comprise buffers, antibiotics, detergents, protease inhibitors and/or enzymes.

Once the nipple areolar complex ECMS has been decellularized 30, a nipple areolar complex ECMS may then be sterilized 40. In one embodiment, the nipple areolar complex ECMS of the present invention is not sterilized, or lacks a sterilization step. In some embodiments which include a sterilization step, the scaffold is sterilized 40 with a combination of peracetic acid and supercritical carbon dioxide or a combination of peracetic acid and ethanol. In some embodiments, the scaffold may be sterilized using gamma irradiation, ethylene oxide, and/or electron beam irradiation. The sterilizing step 40 yields an ECMS that is ready for implantation.

Figure 5A:
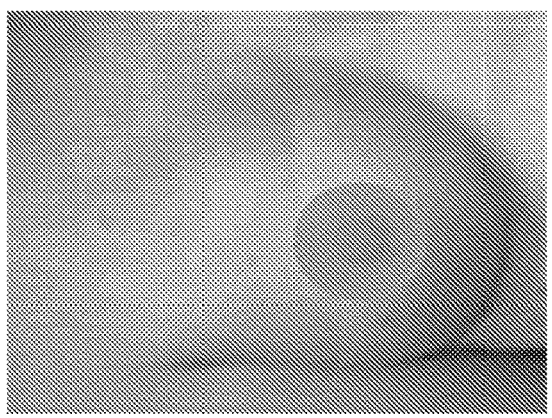
FIG. 5A depicts an illustration of a reconstructed breast mound after mastectomy.
Figure 5B:
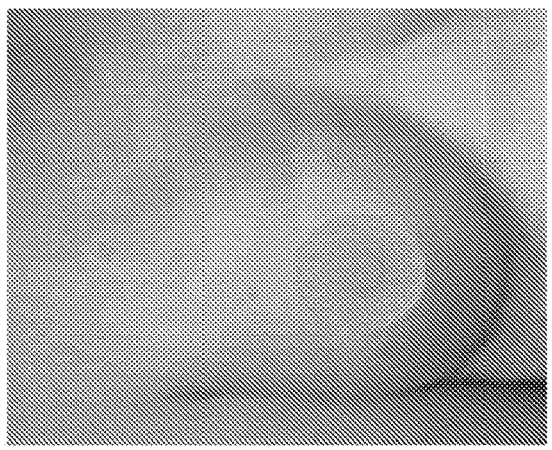
FIG. 5B depicts an illustration of a prepared area for a desired nipple location on the breast.
Figure 5C:
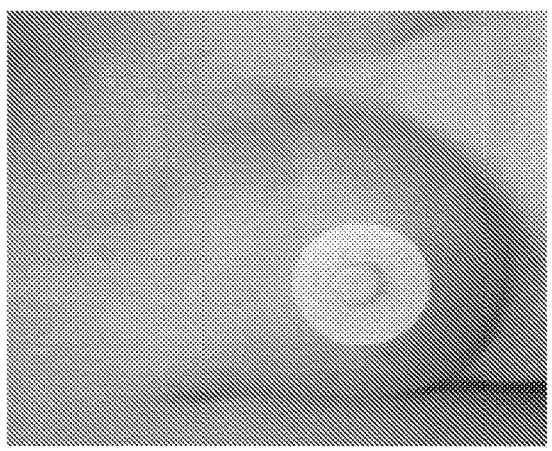
FIG. 5C depicts an illustration of an ECM scaffold of the present invention affixed in the desired location.

In Vivo Recellularization. Turning to FIG. 5A-E, various stages of the regeneration process for the nipple areolar complex comprising the human nipple areolar complex ECMS of the present invention are presented. FIG. 5A provides an illustration of a reconstructed breast mound after mastectomy. FIG. 5B provides a prepared portion of a female breast in a location desired for a nipple areolar complex ECMS of the present invention to be administered. In a preferred embodiment, this occurs by de-epitheliating the skin in the location where the nipple will be located. FIG. 5C presents the administration of a human nipple areolar complex ECMS of the present invention being sutured or adhesively applied to the patient directly. The nipple areolar scaffold may be applied to the recipient directly, whether autologous or allogeneic. The nipple areolar scaffold is then secured in place for incorporation into the donor tissue. May be used alone or in combination with other treatments both cellular and non-cellular deemed appropriate by the physician.

Figure 5D:
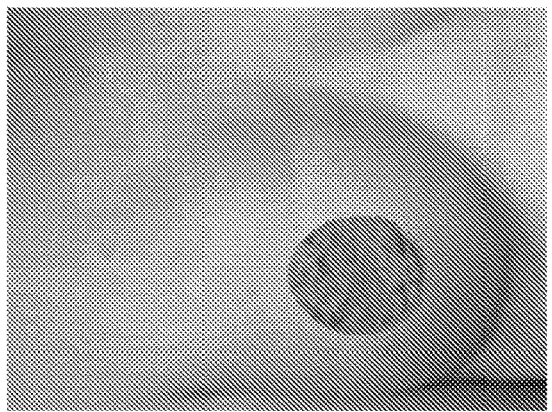
FIG. 5D depicts an illustration of a breast having an ECM scaffold of the present invention having cells repopulated by the patient to create an anatomical human nipple areolar complex.

Blood, plasma proteins, and cells are absorbed into the scaffold allowing cellular access to the scaffold. Neutrophils infiltrate the scaffold and initiate the process of tissue remodeling. Tissue remodeling continues with infiltration of macrophages into the scaffold followed by stem cell recruitment and proliferation within the scaffold. As shown in FIG. 5D, cells from the patient repopulate the nipple areolar complex ECMS of the present invention to create an anatomically correct nipple areolar complex. During the final stages of recellularization, stem cells within the scaffold may differentiate into the appropriate cell types, directed by signaling molecules within the scaffold. FIG. 5E presents the nipple areolar complex ECMS of the present invention wherein the growth factor environment within the ECMS promotes natural pigmentation and improved projection. In an alternative embodiment, additional materials may be added to aid in revascularization of the scaffold such as microvascular fragments isolated from adipose tissue of the recipient.

In another embodiment, the nipple areolar complex ECMS of the present invention is capable of being implanted in a single procedure, and wherein the implantation will lead to cellular incorporation through the patient's innate cellular response.

In Vitro Recellularization. The nipple areolar scaffold may be re-cellularized before implantation using xeno-free culturing methods with cells from the recipient. The cells may include but are not limited to fibroblasts, epithelial cells, mammary endothelial cells, mammary epithelial cells, vascular smooth muscle cells, bone marrow mesenchymal stems cells, adipose derived stem cells, or induced pluripotent stem cells. If using epithelial cells, the cells are isolated from the patient through a skin scraping. The cells will be cultured and expanded in the laboratory using an appropriate medium such as but not limited to keratinocyte serum-free media or other relevant xeno-free medias. Once sufficient cell expansion has occurred, the cells may be lifted for collection by adding a xeno-free cell detachment solution, such as but not limited to ACCUTASE (Stemcell Technologies), TrypLE Select (ThermoFisher Scientific) or ACCUMAX (EMD Millipore), to the media until sufficient cell lifting has occurred. The cells are removed from the tissue culture plate and placed in a conical tube for centrifugation. Total cell count is calculated and appropriate volume of cells and media is added to the scaffold to obtain sufficient cell density per area of scaffold for optimal cell repopulation.

EXAMPLES

The below examples set forth non-limiting embodiments, and for each example, stringency will be modified on how tolerant the tissue is of the various decellularization procedures. These procedures can be used for either autologous or allogeneic tissues.

Example 1

A donor nipple areolar complex (as seen in FIG. 2) is harvested under aseptic conditions with a dermatome, and maintained at low temperature, preferably no warmer than 4° C. The tissue is treated and stabilized for transport with a stabilizing solution. This solution may contain cell culture medium containing 1% penicillin, 1% streptomycin, 1% amphotericin b, 1% antibiotic/antimycotic, 5% heparin, and 2% melatonin. The tissue may stay in the stabilizing solution for no more than 7 days.

The tissue is removed from stabilizing solution and the fat and muscle tissue that remains beneath the human nipple areolar tissue is removed. This may be done immediately or just before processing. The tissue is then placed in a vacuum bag to prevent freezer burn and the excess air is removed.

The tissue is then placed in −30° Celsius and freeze-thawed up to 3 times. The tissue is then placed in a conical tube or Erlenmeyer flask and exposed to 1% sodium dodecyl sulfate (SDS) diluted in PBS or Hanks Balanced Salt Solution while agitated at 175 RPM. The solutions are changed every 12-24 hours. The solutions may also contain 1% antibiotic/antimycotic if deemed necessary. The tissue will be exposed to the decellularization solution for 3-14 days depending on the age of the donor tissue was collected from. The tissue will be agitated in solution at 37±3° C. at 175 RPM. The solution may be changed every 12-24 hours or when solution saturation is reached, whichever comes first. Tissue under the age of 45 years may need to be exposed to decellularization solutions longer due to thicker collagen base of younger human tissue.

After exposure to decellularizing solutions, the tissue is thoroughly rinsed by agitating in deionized or Millipore water at 175 RPM for 3 hours. This process may be repeated 3 times.

Decellularized tissue may be stored in 4° C. or −30° C. either in phosphate buffered saline (PBS) or a vacuum bag until such time as sterilization occurs.

Sterilization is performed by exposing the human nipple areolar ECMS to a mixture of 0.1% peracetic acid and 4% ethanol for up to two hours.

Example 2

A donor nipple areolar complex (as seen in FIG. 2) is harvested under aseptic conditions with a dermatome, and maintained at low temperature, preferably no warmer than 4° C. The tissue is treated and stabilized for transport with a stabilizing solution. This solution may contain cell culture medium containing 1% penicillin, 1% streptomycin, 1% amphotericin b, 1% antibiotic/antimycotic, 5% heparin, and 2% melatonin. The tissue may stay in the stabilizing solution for no more than 7 days.

The tissue is removed from stabilizing solution and the fat and muscle tissue that remains beneath the human nipple areolar tissue is removed. This may be done immediately or just before processing. The tissue is then placed in a vacuum bag to prevent freezer burn and the excess air is removed.

The tissue is then placed in −30° Celsius and freeze-thawed up to 3 times. The tissue is then placed in a conical tube or Erlenmeyer flask and exposed to 1% sodium dodecyl sulfate (SDS), 5% TRITON-X 100, and 1% Ammonium Hydroxide diluted in PBS or Hanks Balanced Salt Solution while agitated at 175 RPM. The solutions are changed every 12-24 hours. The solutions may also contain 1% antibiotic/antimycotic if deemed necessary. The tissue will be exposed to the decellularization solution for 3-14 days depending on the age of the donor tissue was collected from. The tissue will be agitated in solution at 37±3° C. at 175 RPM. The solution may be changed every 12-24 hours or when solution saturation is reached, whichever comes first. Tissue under the age of 45 years may need to be exposed to decellularization solutions longer due to thicker collagen base of younger human tissue.

After exposure to decellularizing solutions, the tissue is thoroughly rinsed by agitating in deionized or Millipore water at 175 RPM for 3 hours. This process may be repeated 3 times.

Decellularized tissue may be stored in 4° C. or −30° C. either in phosphate buffered saline (PBS) or a vacuum bag until such time as sterilization occurs.

Sterilization is performed by exposing the human nipple areolar ECMS to a mixture of 0.1% peracetic acid and 4% ethanol for up to two hours.

Example 3

A donor nipple areolar complex (as seen in FIG. 2) is harvested under aseptic conditions with a dermatome, and maintained at low temperature, preferably no warmer than 4° C. The tissue is treated and stabilized for transport with a stabilizing solution. This solution may contain cell culture medium containing 1% penicillin, 1% streptomycin, 1% amphotericin b, 1% antibiotic/antimycotic, 5% heparin, and 2% melatonin. The tissue may stay in the stabilizing solution for no more than 7 days.

The tissue is removed from stabilizing solution and the fat and muscle tissue that remains beneath the human nipple areolar tissue is removed. This may be done immediately or just before processing. The tissue is then placed in a vacuum bag to prevent freezer burn and the excess air is removed.

The tissue is then placed in −30° Celsius and freeze-thawed up to 3 times. The tissue is then placed in a conical tube or Erlenmeyer flask and exposed to 5% TRITON-X 100 and 1% Ammonium Hydroxide diluted in PBS or Hanks Balanced Salt Solution while agitated at 175 RPM. The solutions are changed every 12-24 hours. The solutions may also contain 1% antibiotic/antimycotic if deemed necessary. The tissue will be exposed to the decellularization solution for 3-14 days depending on the age of the donor tissue was collected from. The tissue will be agitated in solution at 37±3° C. at 175 RPM. The solution may be changed every 12-24 hours or when solution saturation is reached, whichever comes first. Tissue under the age of 45 years may need to be exposed to decellularization solutions longer due to thicker collagen base of younger human tissue.

After exposure to decellularizing solutions, the tissue is thoroughly rinsed by agitating in deionized or Millipore water at 175 RPM for 3 hours. This process may be repeated 3 times.

Decellularized tissue may be stored in 4° C. or −30° C. either in phosphate buffered saline (PBS) or a vacuum bag until such time as sterilization occurs.

Sterilization is performed by exposing the human nipple areolar ECMS to a mixture of 0.1% peracetic acid and 4% ethanol for up to two hours.

Example 4

In an alternative embodiment, sterilization is performed using a combination of peracetic acid and supercritical carbon dioxide ($SCCO_2$) at concentrations and durations optimized for NAC tissue. The sterilization of the NAC extracellular matrix tissue is carried out in a 20-liter pressure chamber which houses wire baskets for holding packaged samples as well as an additive pad to which poly acrylic acid (PAA) (Sigma, ~24-50% vol./vol. PAA in acetic acid) can be added if necessary. The pressure and temperature of the $SCCO_2$ is held constant at 7000-10000 kPa and 30-37° C., respectively, whereas the amount of PAA and the duration of exposure to $SCCO_2$ will be varied. An additive of peracetic acid may be used to ensure sterility if found appropriate from ~10-40% vol/vol in concentration (Sigma Aldrich). The pressure may be held at 7000-10000 kPA at temperatures ranging from 30-37° C. The amount of peracetic acid may vary as well as the duration of tissue exposure (10 to 140 minutes).

Whereas many alterations and modifications of the present invention will no doubt become apparent to a person of ordinary skill in the art after having read the foregoing description, it is to be understood that the particular embodiments shown and described by way of illustration are in no way intended to be considered limiting. Further, the disclosure, examples, and related figures have been described with reference to particular preferred embodiments, but variations within the spirit and scope of the disclosure will occur to those skilled in the art.

In support of the foregoing Examples FIGS. 6-8 present various aspects of the present invention. FIG. 6A presents a histological slice of native human nipple tissue at 200× magnification stained with hematoxylin and eosin. Nuclei are stained evident through purple staining, while the ECM is stained pink. In native human nipple tissue, the cornified keratinocyte layer is visible at the surface with stratified epithelial cells within the epidermis. Melanocytes are primarily localized to the basal layer of the epidermis, although, unique to nipple areolar tissue, some melanocytes are also present within the dermal layers.

FIG. 6B presents a histological slice of human nipple ECM scaffold prepared using Example 1 methods at 200× magnification stained with hematoxylin and eosin. As compared to native human nipple tissue, the nuclei and epithelial cell layers have been removed and only the ECM remains.

Figures 6C, 6D:
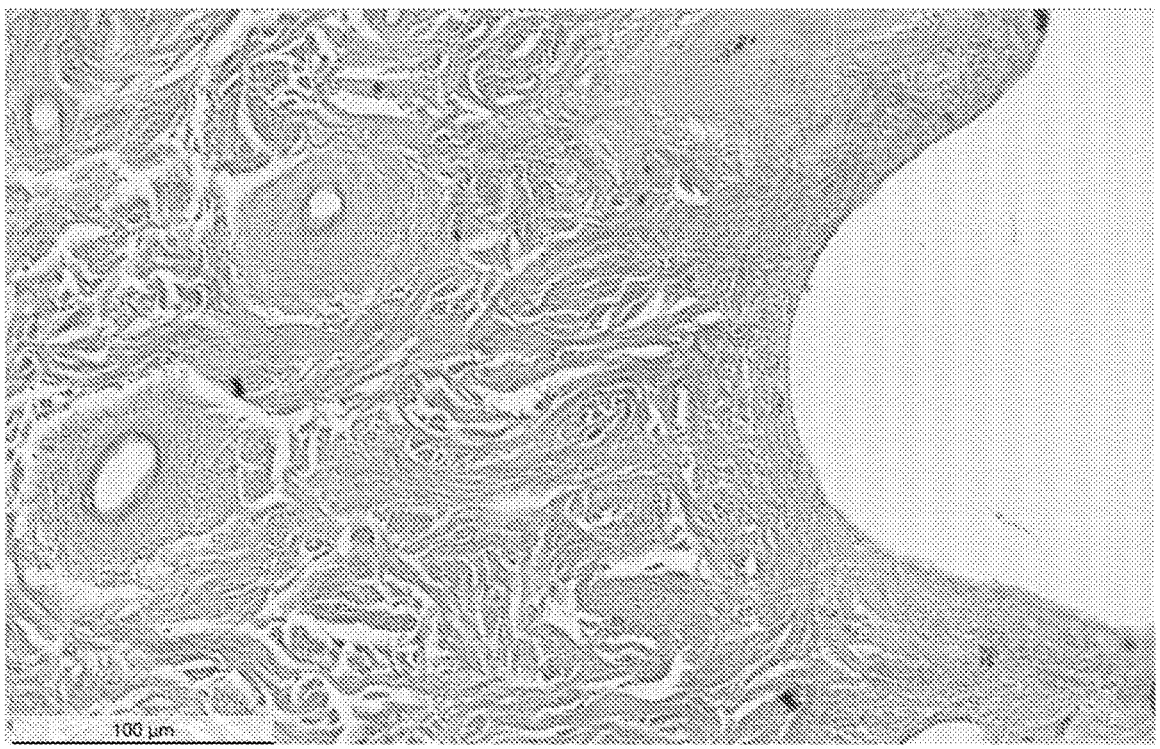
FIG. 6C depicts a histological slice of human nipple ECM scaffold prepared using Example 2 methods at 200× magnification stained with hematoxylin and eosin.
FIG. 6D depicts a histological slice of human nipple ECM scaffold prepared using Example 3 methods at 200× magnification stained with hematoxylin and eosin.
Figure 8A:
FIG. 8 depicts histological stains of native human nipple areolar tissue (left) versus human nipple areolar ECMS (right) at 200× magnification. Trichrome stain was used in FIG. 8A, and FIG. 8E. Hematoxylin and eosin stain was used in FIG. 8B-D and FIG. 8F-8H.
Figure 8A:
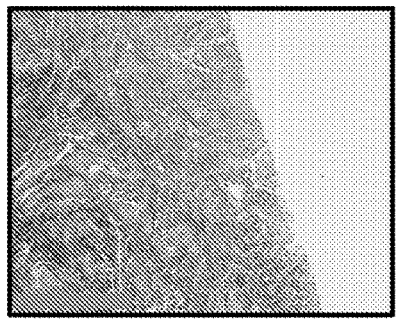
Figure 8B:
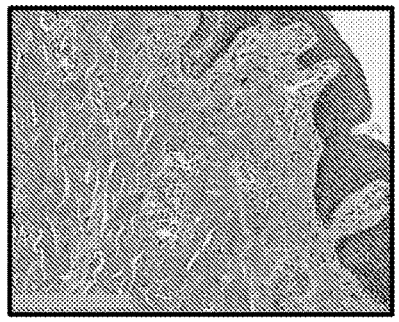
Figure 8B:
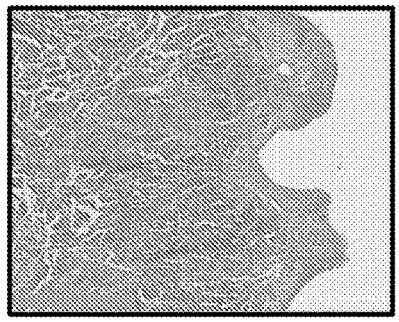
Figure 8C:
Figure 8C:
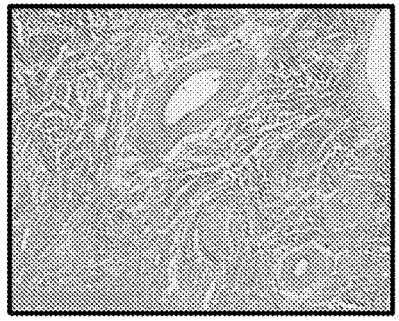
Figure 8D:
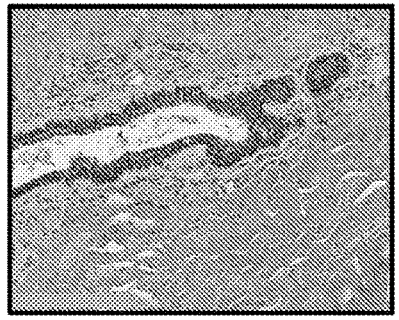
Figure 8D:
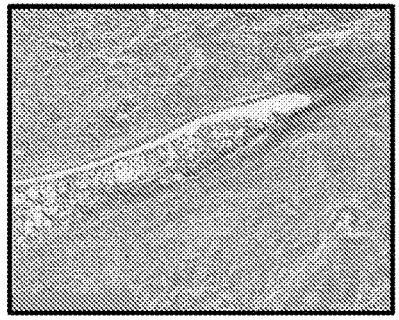

FIG. 6C presents a histological slice of human nipple ECM scaffold prepared using Example 2 methods at 200× magnification stained with hematoxylin and eosin. As compared to native human nipple tissue, the nuclei and epithelial cell layers have been removed and only the ECM remains.

FIG. 6D presents a histological slice of human nipple ECM scaffold prepared using Example 3 methods at 200× magnification stained with hematoxylin and eosin. As compared to native human nipple tissue, the nuclei and epithelial cell layers have been removed and only the ECM remains.

FIG. 7A presents a histological slice of native human nipple tissue at 200× magnification stained with Trichrome Stain. Nuclei are stained black; cytoplasm, muscle, and erythrocytes stained red; and collagen stained blue. The epidermal layer of the tissue is intact, with the epithelial layer removed. FIG. 7B presents a histological slice of human nipple ECM scaffold prepared using Example 1 methods at 200× magnification stained with Trichrome Stain. FIG. 7C presents a histological slice of human nipple ECM scaffold prepared using Example 2 methods at 200× magnification stained with Trichrome Stain. FIG. 7D presents a histological slice of human nipple ECM scaffold prepared using Example 3 methods at 200× magnification stained with Trichrome Stain.

FIG. 8 presents histological stains of native human nipple areolar tissue (left) versus human nipple areolar ECMS (right) at 200× magnification. Trichrome stain was used in FIG. 8A, and FIG. 8E. Hematoxylin and eosin stain was used in FIG. 8B-D and FIG. F-H. Corresponding structures are evident in both the native and decellularized tissue. H&E staining shows unique microstructure of the human nipple is maintained despite cell removal.

It is noted that the foregoing examples have been provided merely for the purpose of explanation and are in no way to be construed as limiting of the present invention. While the present invention has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A method for regenerating a human nipple areolar complex comprising:
   a. harvesting a human nipple areolar complex tissue;
   b. treating the tissue with a stabilizing medium, wherein the stabilizing medium stabilizes the tissue during a transport;
   c. decellularizing the tissue, wherein the cells and DNA are removed, wherein the decellularizing step comprises freezing/thawing the tissue; and
   d. sterilizing the tissue;
   wherein said method yields a nipple areolar complex extracellular matrix scaffold (ECMS) comprised of at least dermal or subdermal layers and wherein the human nipple areolar complex ECMS has reduced immunogenicity in humans as compared to native tissue.

2. The method of claim 1, wherein the harvesting step comprises harvesting the tissue from a human cadaver.

3. The method of claim 1, wherein the harvesting step comprises harvesting the tissue from a human patient during a surgery.

4. The method of claim 1, wherein the decellularizing step comprises decellularization using one or more decellularization methods selected from a group consisting of detergents, enzymes, salts, electrophoresis, and combinations thereof.

5. The method of claim 1, further comprising repopulating the scaffold by cells in vivo after application of the nipple areolar complex ECMS to an individual.

6. The method of claim 5, wherein the step of repopulating the scaffold comprises repopulating the nipple areolar complex ECMS with exogenous cells selected from a group consisting of fibroblasts, epithelial cells, mammary endothelial cells, mammary epithelial cells, vascular smooth muscle cells, bone marrow mesenchymal stem cells, adipose derived stem cells, induced pluripotent stem cells, and combinations thereof.

7. The method of claim 1, wherein the human nipple areolar complex ECMS comprises a basement membrane complex.

8. A method of treatment comprising:
   a. identifying an individual with a need for a nipple reconstruction;
   b. forming a human nipple areolar complex extracellular matrix scaffold (ECMS), the forming comprising:
      i. harvesting a human nipple areolar complex tissue;
      ii. treating the tissue with a stabilizing medium, wherein the medium stabilizes the tissue during transport; and
      iii. decellularizing the tissue, wherein cells and DNA are removed, wherein the decellularizing step comprises freezing/thawing the tissue up to three times; and
   c. sterilizing the tissue;
   wherein said method yields a sterile human nipple areolar complex ECMS comprising at least dermal or subdermal layers; and
   d. applying the human nipple areolar complex ECMS to the individual.

9. The method of claim 8, wherein the individual is an individual who has lost a nipple due to a cancer, a trauma, congenital absence, or a cosmetic reason.

10. The method of claim 8, wherein the decellularizing step comprises decellularization using one or more decellularization methods selected from a group consisting of detergents, enzymes, salts, electrophoresis, and combinations thereof.

11. The method of claim 8, wherein the applying step comprises direct implantation of the ECMS onto the individual.

12. The method of claim 8, wherein the implanted decellularized ECMS is repopulated in vivo by the patient's native cells.

13. The method of claim 8 further comprising, before the applying step, recellularizing the ECMS to yield a recellularized ECMS, wherein the applying step comprises applying the recellularized ECMS to the individual.

14. The method of claim 13, wherein the recellularization of the applying step comprises recellularizing the nipple areolar complex ECMS with exogenous cells selected from a group consisting of fibroblasts, epithelial cells, mammary endothelial cells, mammary epithelial cells, vascular smooth muscle cells, bone marrow mesenchymal stem cells, adipose derived stem cells, induced pluripotent stem cells, and combinations thereof.

15. The method of claim 8, wherein the human nipple areolar complex ECMS comprises a basement membrane complex.

* * * * *